United States Patent
Beyer et al.

[11] Patent Number: 5,119,461
[45] Date of Patent: Jun. 2, 1992

[54] ARRANGEMENT FOR THE ISOTROPIC EMISSION AND ISOTROPIC RECEPTION OF LIGHT

[75] Inventors: Wolfgang Beyer, München; Armin Heinze, Ismaning; Eberhard Unsoeld, Oberschleissheim, all of Fed. Rep. of Germany

[73] Assignee: Gesellschaft für Strahlen- und Umweltforschung mbH, Neuherberg, Fed. Rep. of Germany

[21] Appl. No.: 620,898

[22] Filed: Dec. 3, 1990

[30] Foreign Application Priority Data

Dec. 18, 1989 [DE] Fed. Rep. of Germany ....... 3941706

[51] Int. Cl.⁵ .............................................. G02B 6/26
[52] U.S. Cl. .................................... 385/147; 385/123; 385/902

[58] Field of Search ............... 350/96.29, 96.10, 96.15, 350/96.20, 96.30, 96.18; 385/12, 13, 122, 31, 123, 128, 147, 902

[56] References Cited

U.S. PATENT DOCUMENTS

| | | | |
|---|---|---|---|
| 4,660,925 | 4/1987 | McCaughan, Jr. | 350/96.15 |
| 4,693,556 | 9/1987 | McCaughan, Jr. | 350/96.18 X |
| 4,770,488 | 9/1988 | Shank et al. | 350/96.18 X |
| 4,844,580 | 7/1989 | Lynch et al. | 350/96.18 |

Primary Examiner—John D. Lee
Assistant Examiner—Phan T. Heartney

[57] ABSTRACT

Apparatus for the isotropic emission and for the isotropic reception of light which includes a light conductor having a conical distal end with a scattering body mounted thereon in spaced relationship such that a cavity is formed between the light conductor end and the scattering body. The apparatus permits access to cavities such as hollow organs for internal laser phototherapy, for example.

5 Claims, 3 Drawing Sheets

ARRANGEMENT FOR THE ISOTROPIC EMISSION AND ISOTROPIC RECEPTION OF LIGHT

BACKGROUND OF THE INVENTION

Field of the Invention

The invention relates to an arrangement for the isotropic emission and the isotropic reception of light which includes a light conductor with a light emitting end provided with a light scattering structure.

Description of the Prior Art

In such arrangements the distal end of the light conductor generally has a light scattering body of low light absorption characteristics mounted on the flat end thereof.

The light conductor generally emits from its end an axially symmetric divergent light beam (with maximum divergence or acceptance angle of common glass fibers being about 30°). Photons entering the scattering body change their direction frequently depending on the length of their path and the density of the scattering body. Ideally, this would lead to a fully scattered light emission.

With isotropic detectors, photons from any spatial direction enter a spherical scattering body in which they lose their original direction. Photons which meet the plane light conductor end face at the acceptance angle of the light conductor face or a smaller angle will enter the light conductor.

Development of all emitters and detectors of light radiation is based on this principle. Only the design of the scattering bodies and their mounting on the light conductors was subject to variations; the geometry of the end face of the light conductor has never been studied with a view to influencing the emission and detection characteristics in a particular way.

U.S. Pat. No. 4,693,556, McCaugham, Jr., relates to a process for the manufacture of a light scattering device wherein a light scattering medium consisting of a mixture of powdered quartz and an adhesive is applied in several layers to the flat end face of a fiber conductor core. Several layers of the mixture are applied and cured by UV light exposure thereby forming a light scattering body at the end of the fiber.

In the article "Advances in Laser Medicine, Safety and Laser Tissue Interaction" (Editors: G. J. Miller and H. P. Berlien), Ecomed, Lansberg, 1989, pages 358-368, W. M. Star and J. P. A. Marijnissen describe the manufacture of isotropic detectors consisting of plastic spheres which are provided with bores and adhesively mounted onto the ends of light conducting fibers.

In "Photodynamic Therapy of Tumors and other Diseases" (Editors: G. Jari, C. Perria), Liberia Progetto Editore Padova, 1985, pages 371-385, V. Russo describes light conductors with conical distal ends. The article is concerned only with radial, that is, annular, light emission. There is no mathematical relation given between the cone angle and emission characteristics. (The etching procedure utilized for the manufacture of the conical ends provides for badly reproducible conical ends in any case.)

With all known arrangements, the axially directed light emission characteristic of a light conductor is converted to a spherically symmetric characteristic in only an incomplete manner. Particularly critical is the much too ineffective light emission to the rear hemisphere with respect to the direction of light travel through the conductor. The reasons herefor are:

Shading by connecting elements between the light scattering body and by the light conductor itself. (Connecting elements are needed, for example, if the light transmission density of a light receiving surface area of the scattering body must be reduced by an increase of the distance between the light conductor and the scattering body.)

Only limited optimization capability of the light refraction is available if the scattering body dimensions (endoscopic uses) and the absorption losses (overheating of the scattering body) are to be small.

Common isotropic emitters (with a diameter of 3-4 mm) are too large for most endoscope and catheter channels. A reduction of emitter dimensions is therefore highly desirable. At the same time, however, light emission capabilities of at least 2 W are required but neither of these objects can be achieved with the planar conductor end faces presently used since the emission characteristics would deteriorate to an unacceptable degree as a result of high light density.

Also the known isotropic detectors have a relatively low sensitivity.

Compared to the surface of the scattering body, light conductors with planar fiber ends provide for a relatively small face area through which photon-s may enter only within a relatively narrow incident angle of maximally 30°.

In order to provide for sufficient light refraction in the scattering body, the scattered light density must be selected so as to be sufficiently high such that a large part of the incident light is reflected from the scattering body.

It is the principal object of the present invention to provide an apparatus including a light conductor for the irradiation of, and light detection in, cavities which are difficult to access, for example, for medical laser applications such as the internal photodynamic therapy of hollow organs wherefor the apparatus should be small in diameter but should have very good spherical light emission characteristics.

SUMMARY OF THE INVENTION

The object is achieved by an apparatus which consists of a coated light conductor provided with a conical distal end disposed in a cavity formed in a scattering body which is firmly mounted on the conductor. The cavity is large enough such that light conductor end surfaces are spaced from the cavity walls.

Preferably the scattering body is a hollow sphere or at least it has a cylindrical cavity into which the light conductor extends. The cone at the light conductor is shaped depending on the desired light distribution through the scattering body. It may be, for example, in the form of a truncated cone.

The apparatus according to the invention achieves the following advantageous results:

The scattering body is functionally relieved since it is only required to smoothen the radiating and detecting characteristics of the light conductor tip.

The total amount of refractions for the generation of a spherically symmetric emission or detection is relatively small.

The resulting relatively small density of stray radiation provides for relatively low absorption losses in the scattering body and consequently a relatively high threshold for defects caused by overheating.

Relatively small detection losses caused by reflections on the scattering body's surface.

In contrast to a planar fiber conductor end face, the conical conductor end provides for the irradiation of a substantially larger area, for example, a cylindrical bore in the scattering body. A reduction of radiation density by a light conductor mounting structure arranged near the light emitting conductor surfaces can therefore be avoided. Back shading is limited to the area of the light conductor itself and consequently is minimized.

Compared with conventional arrangements the present invention provides for small equipment dimensions and homogeneous radiation characteristics with a similar or higher level of load capacity.

The conical conductor end is capable of detecting light radiation with a large range of incident angles and consequently has a substantially greater sensitivity than a conductor with planar end face.

If necessary the cone angle can be adjusted appropriately for preferred irradiation of the rear hemisphere. This is advantageous if, as a result of integration of the scattering body with a catheter, increased shading of the rear areas by the catheter is to be expected.

During the internal photodynamic therapy after tumor selective enrichment of photosensitizers in the organ walls, a homogeneous light dose is applied to the organ walls—tumors and healthy tissue. The required homogeneous illumination can best be obtained in spherically shaped organs such as the bladder by way of isotropic emitters with an approximately spherical emission pattern.

Taking chemical experiences into consideration, an isotropic emitter should satisfy the following requirements:

The emission characteristics should be as homogeneous as possible for the various sectors; asymmetries particularly concerning the rear cavity wall areas should be avoided.

The output under continuous service should be at least 2 Watts in order to permit application of the required light energy within an acceptable treatment period.

It should be possible to incorporate the radiation emitter in clinical endoscope or catheter systems, that is, it should have a self-supporting scattering body of less than 3 mm diameter.

For simulations in laboratory arrangements, low power, optimum emission characteristics and—depending on the application—minimal dimensions are required.

SHORT DESCRIPTION OF THE DRAWINGS

FIGS. 1 and 2 show different embodiments of the arrangement according to the invention; and FIG. 3 is an enlarged cross-sectional view of the distal end of the light conductor.

DESCRIPTION OF THE PREFERRED EMBODIMENTS

Figure 1:
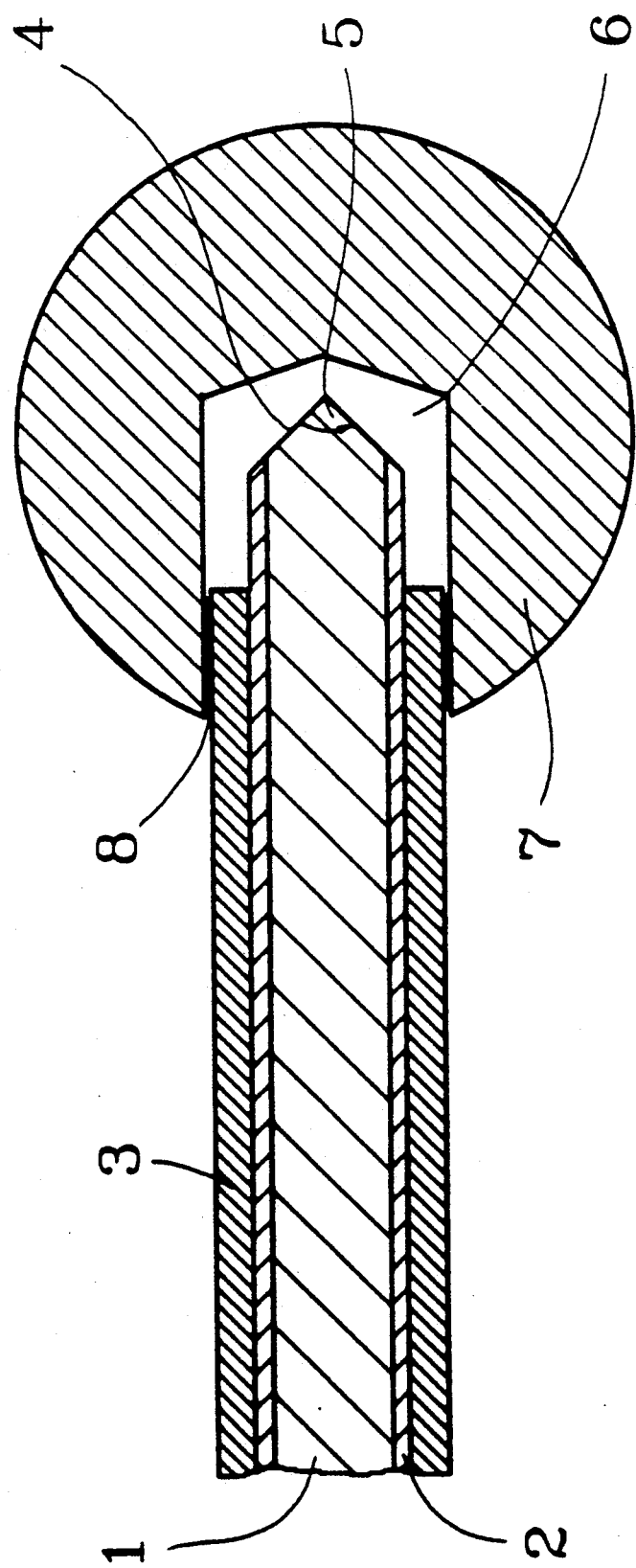
Figure 2:
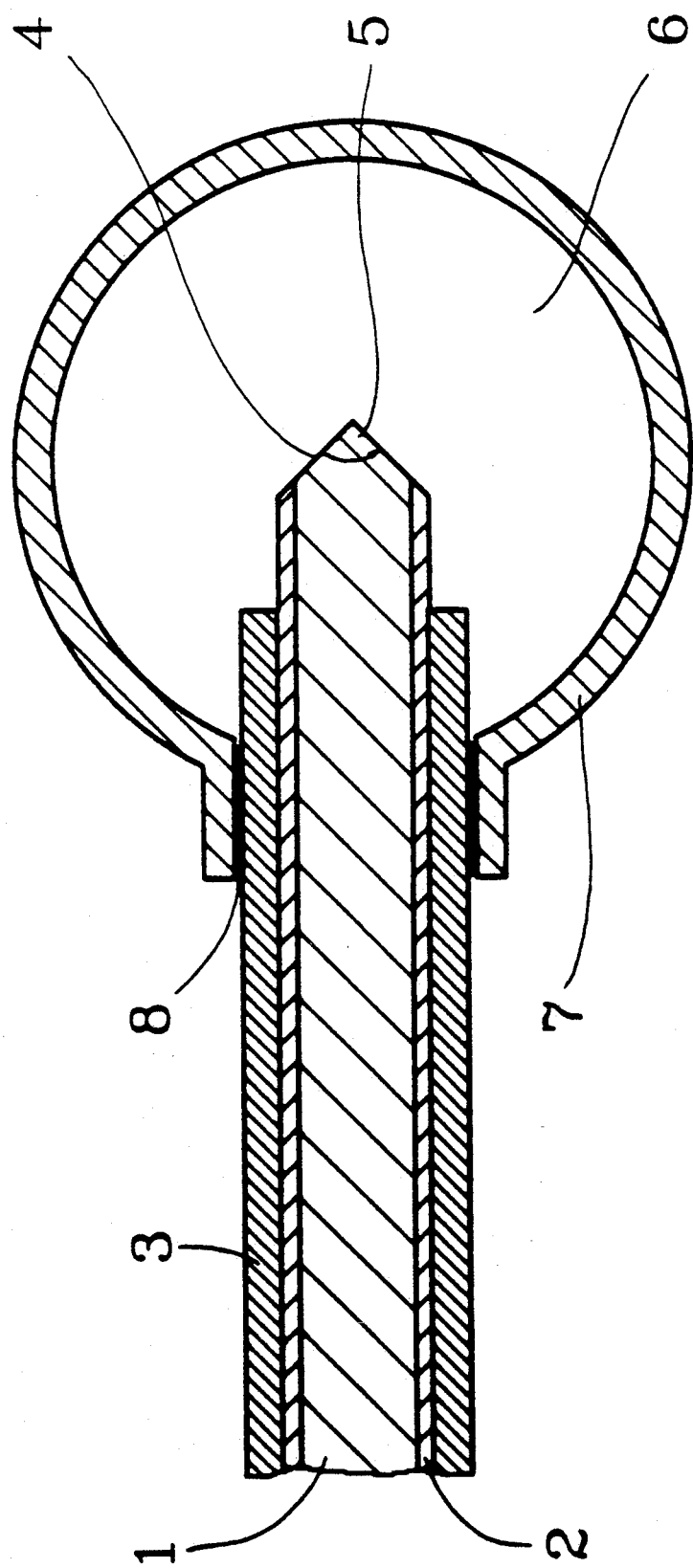

FIGS. 1 and 2 show a light conductor with a core 1, a cladding 2 and a coating 3, wherein the distal end face 4 of the light conductor has the shape of a cone or a truncated cone, each with a cone angle 5. A medium 6 surrounds the light conductor end which medium is optically thin in comparison to the light conductor. A scattering body 7 is mounted onto the light conductor coating 3 by way of connecting means 8.

The scattering body is self supporting and consists of a support material (such as plastic, glass or a compound material) and a scattering compound (for example, $BaSO_4$ or $TiO_2$) and its diameter is less than 5 mm. The size relation of scattering body to light the conductor coating diameter is larger than 2.

Embodiment I (FIG. 1) shows an arrangement with a solid scattering body with an opening at one end for the reception of the light conductor; and Embodiment II (FIG. 2) shows an arrangement with a hollow, preferably spherical, scattering body with a tubular guide for the reception and the support of the light conductor.

The scattering body 7 has the following optical characteristics:

EMBODIMENT I

| | |
|---|---|
| Absorption in body 7: | <10% |
| Back scattering from body 7 into the medium 6: | <50% |
| Light transmission through the body 7: | >50% |

EMBODIMENT II

| | |
|---|---|
| Absorption in body 7: | <10% |
| Back scattering from body 7 into medium 6: | >50% |
| Light transmission through the body 7: | <50% |

The required index of refraction of the medium 6 depends on the index of refraction of the conductor core 1. The refraction index ratio of the conductor core relative to the medium 6 must be larger than 1.3.

The conical end 4 of the light conductor 1, 2, 3 provides for controllable light emission into the forward (emission angle relative to the light conductor axis: $\beta a < 90°$) and the rear hemisphere ($\beta a > 90°$).

The distribution of light to the two hemispheres which depends on the cone angle 5, the travel direction distribution of the photons before contact with the first interface (represented by the angle between the photon path and the light conductor axis and the ratio of the refraction indices $n_1$ and $n_6$ of the light conductor core) and the medium 6 can be achieved as follows:

Assuming that the light conductor core 1 is optically denser than the surrounding medium 6, either of two phenomena may occur at the interface:

1. Refraction: the photon passes through the interface but changes its direction in accordance with the law of refraction.

2. Total reflection: the photon remains in the light conductor but changes its direction in accordance with the law of reflection.

The limiting angle for total reflection $\alpha g$ and the incident angle $\alpha 10$ of the photon path relative to a line normal to the interface determines which phenomenon occurs. Conditions for:

Refraction $|\alpha| \leq \alpha g$ (1)

Total reflection $|\alpha| > \alpha g$ (2)

Figure 3:
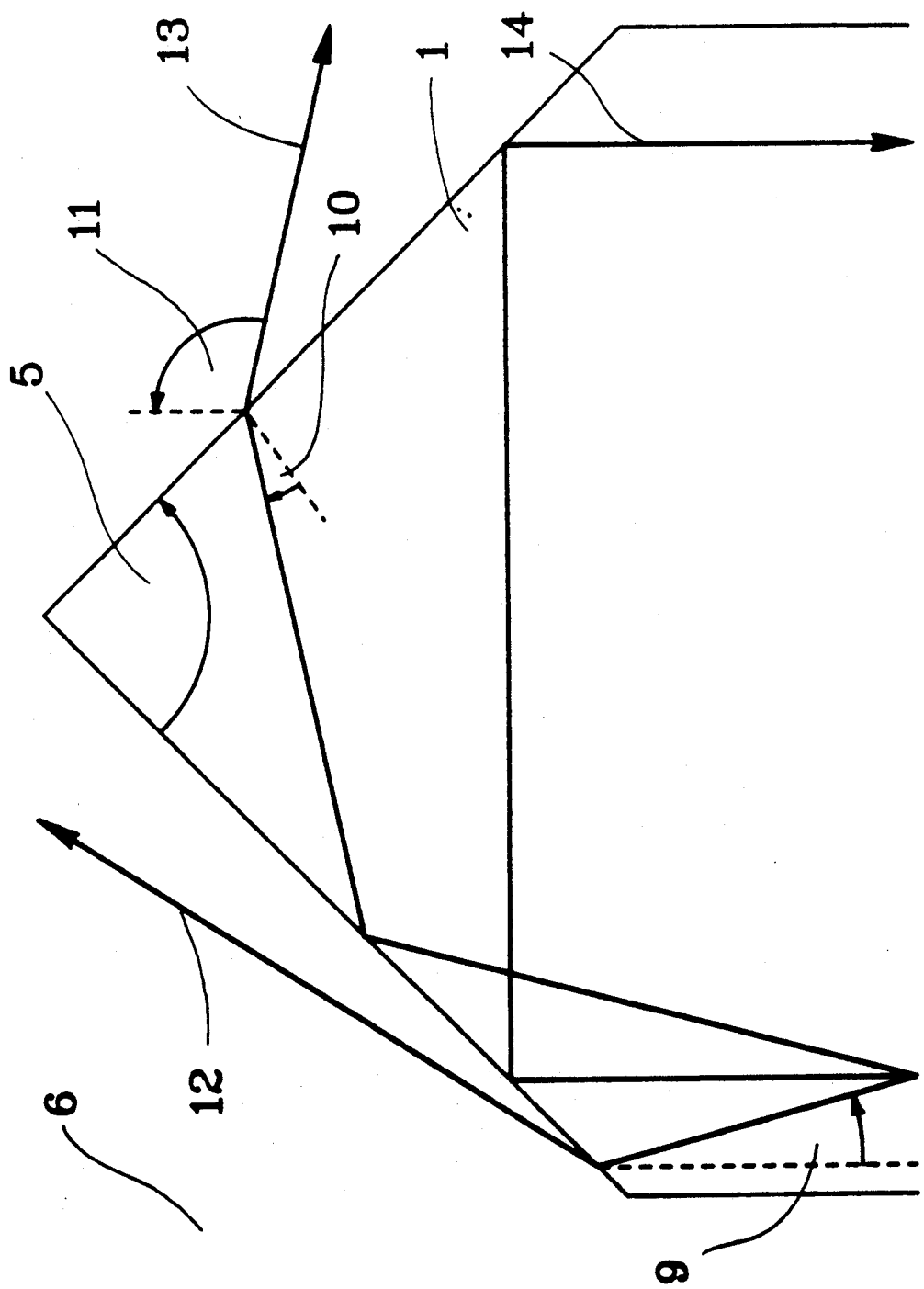

In conical light conductor ends the incident angle $\alpha$ at the $n^{th}$ interface contact (two-dimensional model) is:

$$\alpha = 90° - \phi - \delta/2 \times (2 \times n - 1) \quad (3)$$

wherein:

$\phi$ is the angle between the photon path and light conductor axis before the first interface contact (positive sign photon path departs from the light conductor axis, negative-vice versa; FIG. 3: numeral 9').

$\delta$ is the cone angle 5 (angle between the opposite cone generatrices).

Conditions for the emission angle 11 $\beta a$:

$$\beta a = 90° - \delta/2 - \arcsin(n_1/n_6 \times \sin \alpha)$$

Of particular importance in connection with the present invention are the beam paths 12, 13 and 14 shown as examples in FIG. 3.

Under conditions a) and b) it is determined:
a) cone angle limits: $80° \leq \delta \leq 90°$ b) ratio of the refraction indices: $n_1/n_6 > 1.3$ Light path 12 = primary refraction (n=1):

$$\alpha \leq \alpha g \quad 0 \leq \beta a \leq \delta$$

These conditions result in emission into the forward hemisphere.

Light path 13 = primary total reflection (n=1), secondary refraction (n=2):

$$n=1: \alpha > \alpha g$$

$$n=2: |\alpha| \leq \alpha g, \text{ ca. } 70° < \beta a < \text{ca. } 135°$$

This part of the radiation illuminates only the rear hemisphere or both hemispheres depending on parameter selection.

Light path 14 = primary total reflection (n=1), secondary total reflection (n=2):

$$n=1: \alpha > g\alpha$$

$$n=2: |\alpha| > \alpha g, \alpha \text{ negative}$$

This part is reflected back into the light conductor and is lost.

By variation of the angle 5 ($\delta$) the beam angle distribution in the light conductor (that is, the availability of angles 9) and the fraction index change 1, 6 the total photon flow through the light conductor can be distributed to the light paths 12, 13 and 14 in a controlled manner.

The conical light conductor end consequently permits to provide for predetermined appropriate light distribution to both hemispheres depending on the characteristics of the scattering bodies.

With the conditions a) and b) (see above) a desired margin between the rear and forward distribution ratio v of $1 < v < 3$ can be achieved:

For an increase of light emission to the forward hemisphere, for example, the conical light conductor end 4 may be provided with a rounded or truncated portion.

For isotropic detectors the same considerations apply as for isotropic light emitters with regard to the scattering bodies 7. With regard to the light conductor ends the following considerations apply:

Photons can enter the light conductor at the conductor end within a large range of incident angles and consequently can be detected within a wide incident angle range.

The light beam paths 12 and 13 as shown for an isotropic emitter are reversible, light beam path 14 does not occur (geometry as in FIG. 3).

Detection angle $\beta e$ (corresponding to 11) under conditions a) and b) (see emitter):

1: $0° < \beta e < \delta$ with N.A. = 0.4

(N.A. = numerical aperture of the light conductor)

2: ca. $70° < \beta e < $ ca. $135°$ with N.A. = 0.4

The detection rates of the beam paths 12 and 13 for photons which arrive at the cone surface depend on the orientation distribution of the photons—that is, indirectly on the optical properties of the scattering body—on the numerical aperture of the light conductor, on the cone angle 5 ($\delta$) and on the difference of the indices of refraction of the light conductor 1 and the adjacent medium 6.

By appropriate selection of the above parameters, the detection characteristics can be optimized.

In summary, the present invention is concerned with the combination of a cone-shaped light conductor end with a scattering body wherein emission or detection characteristics of the arrangement can be selectively determined by appropriate determination and selection of the cone angle as required for a desired result.

LISTING OF REFERENCE NUMERALS

1 Light conductor core
2 Light conductor cladding
3 Light conductor coating
4 Light conductor end face
5 Light conductor cone angle
6 Medium
7 Scattering body
8 Connecting means
9 Angle between photon path and light conductor axis before the first interface contact
10 Incident angle with respect to a line normal to the interface
11 Emission angle and detection angle with regard to the light conductor axis
12 Light path—primary refraction
13 Light path—primary total reflection, secondary refraction
14 Light path—primary total reflection, secondary total reflection

What is claimed is:

1. Apparatus for the isotropic emission or reception of light, said apparatus comprising a light conductor having a conical distal end surface and being provided with a coating and a scattering body having a cavity receiving the distal end of said light conductor and being connected to the coating on said light conductor, said cavity being sufficiently large so as to provide for some space between the light conductor end surface and the cavity walls of said scattering body.

2. Apparatus according to claim 1, wherein said scattering body is a hollow sphere.

3. Apparatus according to claim 1, wherein said scattering body is a sphere having formed therein a cavity receiving the end of said light conductor.

4. Apparatus according to claim 1, wherein said light conductor end is in the form of a truncated cone.

5. Apparatus according to claim 1, wherein said light conductor has a predetermined refraction index and any medium in the space surrounding the light conductor end has a refraction index, said conductor and said medium having a refraction index ratio which is larger than 1.3.

* * * * *